United States Patent [19]

Howell

[11] 4,380,257

[45] Apr. 19, 1983

[54] METHOD AND APPARATUS FOR PROCESSING FLUID MATERIALS

[75] Inventor: Gary W. Howell, Newark, Del.

[73] Assignee: E. I. Du Pont de Nemours and Company, Wilmington, Del.

[21] Appl. No.: 230,386

[22] Filed: Feb. 2, 1981

[51] Int. Cl.³ .......................... B65B 3/04; B67C 5/37
[52] U.S. Cl. ...................................... 141/1; 141/392; 193/15; 248/562; 425/261
[58] Field of Search ..................... 141/130, 250–284, 141/369–389, 391, 392, 1–12; 248/562; 193/15; 425/261, 447

[56] References Cited

U.S. PATENT DOCUMENTS 376,531   1/1888   Lentz ...................................... 193/15
3,268,199  8/1966   Kordyban et al. ................... 248/562

Primary Examiner—Houston S. Bell, Jr.

[57] ABSTRACT

Samples of body fluids such as blood, urine, etc. are passed for analysis through separating columns to extract the desired component from the raw sample. Unwanted ingredients of the sample flow through the resin bed to a refuse cup. The retained desired component is later released from the resin bed by a solvent and collected in a recovery cup. Fluids passing through the resin bed are selectively passed to the refuse cup or recovery cup by flexing a disklike support for the resin bed. Preferably the support is flexed by applying a differential gas pressure across the support.

An apparatus for implementing this method includes in a flexible disk, adapted to hold separating columns, suspended across an opening of a vacuum chamber. The outside edges of the disk form a seal for the chamber. The separating columns are in vertical alignment with waste receptacles disposed in a second disk positioned below the first disk. Differential pressures established across the flexible disk cause fluids to flow through the columns and, when sufficient differential pressure is applied, the disk flexes. When the disk flexes, the lower tips of the separating columns extend outward radially to align with the recovery cups. Hence fluid switching is attained and the flow through the separating columns is switched from the waste cups to the recovery cups.

21 Claims, 4 Drawing Figures

METHOD AND APPARATUS FOR PROCESSING FLUID MATERIALS

BACKGROUND OF THE INVENTION

This invention relates to processing fluid materials and, more particularly, to a method and apparatus for fluid switching.

Fluids are processed in many different fields for many different applications. It is often necessary or desirable in the processing of fluids to switch from one flow path to another. For example, one may wish to filter fluids, to determine different components or constituents of a sample, to separate fluids, to concentrate fluids, and the like. In each of these applications, the fluids often must be passed through different separating media, filters or dividers. It is also often necessary or desirable in the processing of fluids to utilize centrifugal force or a vacuum as the mechanism for enhancing fluid flow.

For example, in the analysis of samples, particularly biological samples, such as whole blood, serum or urine, one must separate or extract the desired components from the sample for later analysis. Analytical procedures that typically require this step include trace organic and inorganic analyses for environmental control in such areas as monitoring industrial effluents, pesticide run-off in drinking water, impurity and formulation analyses in the food and pharmaceutical industries, and process monitoring in many industrial operations. Typically, these analyses require that the extraction or separation step of the desired sample component be performed manually. Once the extraction is made, the extracted or separated components can be analyzed by any known analytical technique such as thin-layer chromatography, mass spectrometry, gas chromatography, and the like.

One such extraction technique is described by Quame in U.S. Pat. No. 3,567,029. Quame describes the use of a disposable separating column filled with a particular solid phase, capable of extracting certain lipophilic compounds, including the most commonly encountered abused drugs, such as phenobarbital, amphetamine, methadone and the like. In a typical drug extraction, such as from a urine sample, Quame allows the urine sample to pass through the column. The column selectively adsorbs any lipophilic drugs contained in the urine, thereby extracting the lipophilic drugs from the aqueous phase which is passed to a waste receptacle. The receptacle is manually replaced by a recovery cup. Next, the adsorbed drugs are eluted from the column by a solvent which is passed to the recovery cup. This technique works quite well for some urine samples. Unfortunately, however, it is somewhat time consuming because it is manual and because the sample and the solvent phases are slow to pass through the column and filter combination. The application of a vacuum has been used to speed up the flow, but even here required manual switching between different fluids and of the waste receptacle and recovery cup poses a problem.

Another technique for assaying fluids is that described by Shapiro et al. in U.S. Pat. No. 3,953,172. Shapiro uses a swinging bucket centrifuge rotor with the buckets each holding a separating column. The fluid samples to be assayed are mixed with a reagent at the central part of the centrifuge rotor and then allowed to pass, under the influence of centrifugal force, through the separating column. While Shapiro does have the advantage of using centrifugal force to speed up the process, he is still limited somewhat in application, as are the vacuum techniques, in that multiple fluids cannot readily be used to recover the desired sample components from the column. It is even more difficult to concentrate the desired materials for later analyses. No fluid switching is provided, i.e., no means is provided to permit different fluids flowing through a separating column to pass to different collecting vessels. Conceivably, this might be accomplished by various valving arrangements, but such becomes relatively complex and, in any event, apparently has never been accomplished.

CROSS-REFERENCE TO RELATED APPLICATION

This invention is related to the invention described in U.S. Pat. No. 4,190,530, issued Feb. 26, 1980 entitled Centrifugal Method and Apparatus for Processing Fluid Materials, which discloses a centrifugal fluid switching technique.

SUMMARY OF THE INVENTION

According to this invention, a raw sample is prepared for further analysis by passing it through a separating column having an affinity for a desired constituent of the sample. Unwanted ingredients of the sample flow through the separating column into a waste receptacle or cup. The retained sample may be released from the column by a solvent and collected in a recovery cup separate from the waste cup. To achieve this recovery, it is necessary to switch the fluid exiting from the column between the respective waste and recovery cups.

The method of this invention facilitates such switching by controlling the flow of a fluid from a first (the separating column) to second (the waste cup) and third (the recovery cup) unconnected flow paths. This is accomplished by positioning the first flow path in a generally planar member, positioning second and third flow paths in side by side relation vertically below the first flow path, and flexing the member, as by applying a differential gas pressure across the member, to switch the alignment of the first flow path from one to the other of the second and third flow paths.

In the first instance, the passage of fluid from the first to the second and third flow paths is enhanced by applying a differential pressure across the member. The member flexes when the differential pressure is increased to a value greater than the differential pressure normally used for passing the fluid through the column.

Apparatus for effecting the method of this invention includes a flexible, generally planar support defining a receptacle for removably positioning a first flow device, first rack means for removably positioning second and third flow devices in side by side relation, one of the second and third devices being vertically below and in flow alignment with the first member, and means to flex the support to tip said first device into flow alignment with the other one of the second and third devices.

Preferably the means to flex includes means to apply differential pressure across the support. Additionally means are provided to damp the flexure movement of support. Such means may include a dashpot integrally connected to the support.

The flexible support may be part of an assembly including the support and a lower disk which may function in a vacuum chamber as a dashpot to prevent too rapid a movement of the support. This structure may be adapted to fit within a vacuum chamber with a fluid distributor disposed above to pass the various fluids through the flow paths.

BRIEF DESCRIPTION OF THE DRAWINGS

Further advantages and features of this invention will become apparent from the following description wherein.

DETAILED DESCRIPTION OF THE PREFERRED EMBODIMENT

This invention facilitates processing fluid materials by using changes in air pressure. The fluid materials are placed in a first flow path which may include a filter, a separating column or other device which affects the fluid materials physically or chemically. The sample materials are forced through the first flow path by the use of a differential pressure applied across the ends of the flow path. Unwanted ingredients of the sample material pass through the flow path and are directed into a waste receptacle or cup, i.e., a second flow path. The sample material of interest that is retained in the filter or column is later released by a solvent and collected in a recovery cup, i.e., the third flow path. The solvent may be evaporated leaving the sample in a dried form.

According to the method of this invention, upon exiting from the first fluid flow path, the sample material or the processed fluid materials may be switched to pass to either second or third fluid flow paths. The second and third fluid flow paths may be simple cups as noted. The flow paths, being disconnected, may be switched to pass the materials from the first flow path to either the second or third flow paths. By changing the differential pressure along the flow paths, both passage through the first flow path and flexure of a disk is achieved. Switching is accomplished by allowing the disk to flex or collapse at a predetermined pressure differential. As the disk collapses or concaves, the lower tips of the first flow paths, which may be separating columns, initially in alignment with the waste cups, extend outward radially to align with the recovery cups.

To effect the method of this invention, the first flow path is positioned in a flexible, generally planar divider member or disk. The outlet of the first flow path is aligned vertically above one of the second and third flow paths, which are positioned in side by side relation. A differential gas pressure applied across the divider member, and hence across the first flow path, aids in causing liquid to flow through the first flow path. Finally, the divider is flexed by applying a somewhat greater differential gas pressure across the divider thus to align the outlet of the first flow path with the other one of the second and third flow paths. In many applications the first flow path will constitute a separating column and the differential pressure used to flex the divider is greater than the differential pressure used to pass the fluid through the first flow path.

Figure 1:
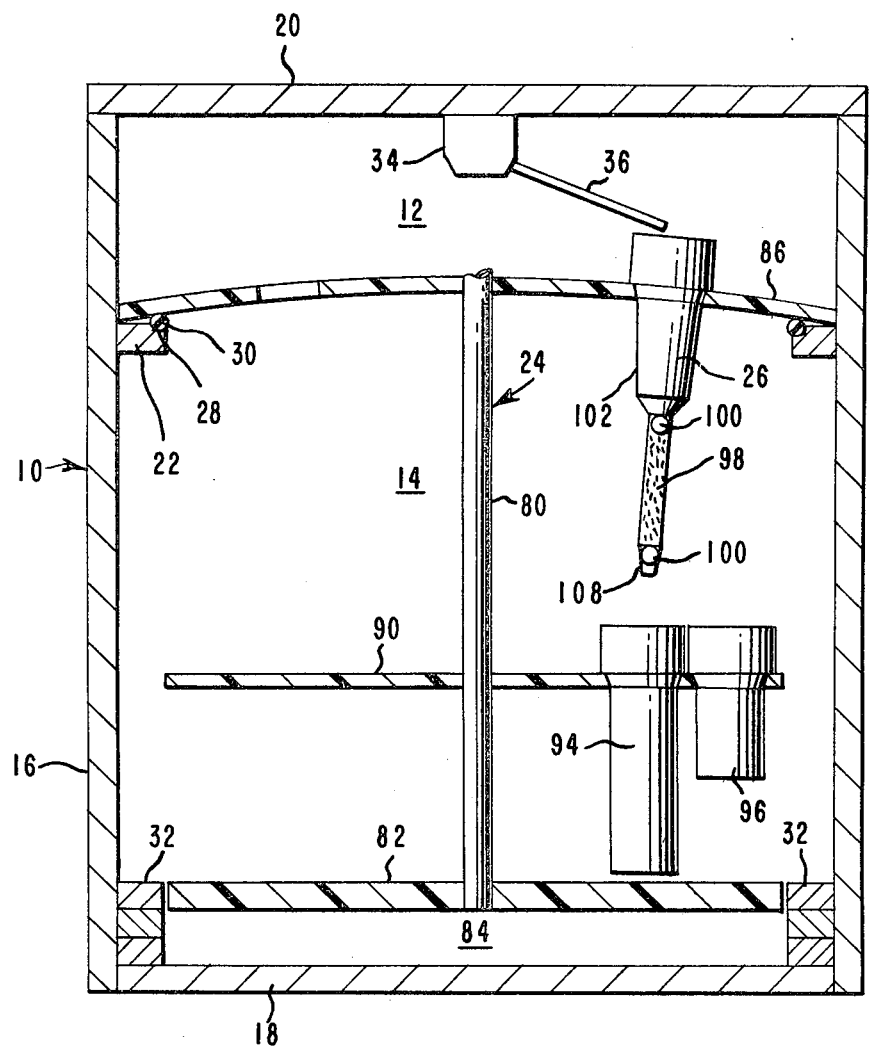
FIG. 1 is a cross-sectional elevation view of a fluid switching apparatus constructed in accordance with the preferred embodiment of this invention.
Figure 2:
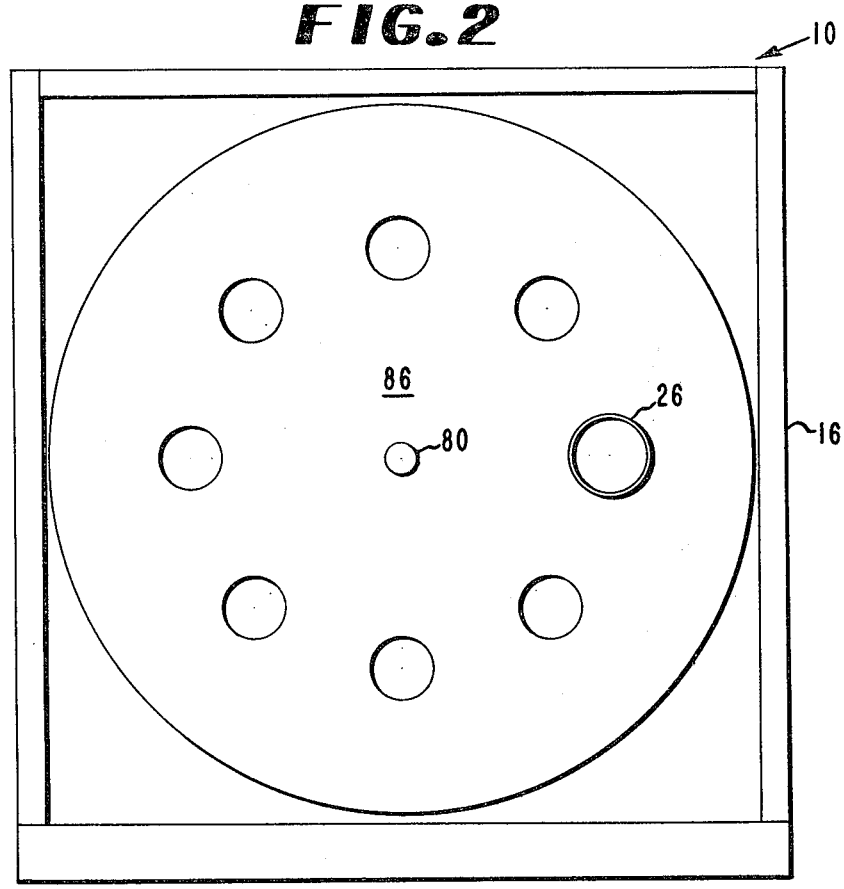
FIG. 2 is a plan view of the fluid switching device depicted in FIG. 1.
Figure 3:
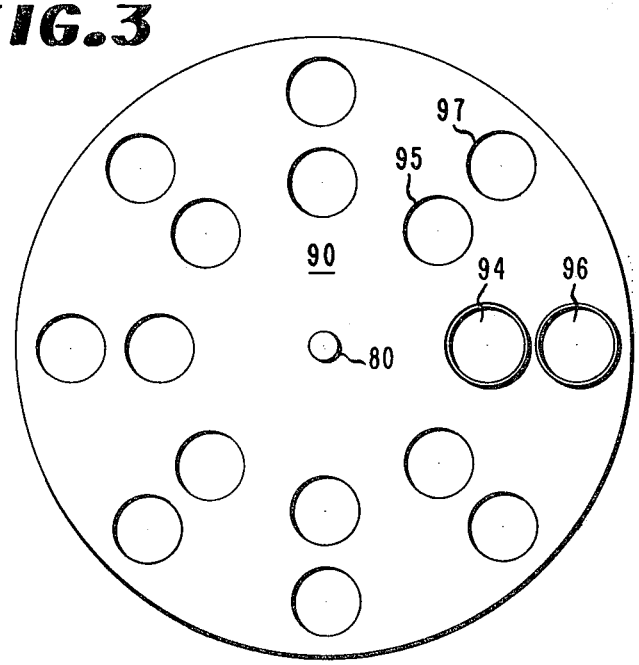
FIG. 3 is a plan view of a lower support in the fluid switching apparatus.

A preferred apparatus that may be used to implement the method set forth above is that depicted in FIGS. 1, 2 and 3. As may be seen in FIGS. 1 and 2, in particular, there is a housing 10 which includes an upper section or vacuum chamber 12 and a lower section or vacuum chamber 14. This housing 10, as may be seen, is generally cylindrical in shape with walls 16 formed of any suitable rigid material such as aluminum or stainless steel. The housing 10 is a sealed unit with a base member 18 and a removable lid 20 both also formed of the same material as the housing 10.

An inner flange 22 located on the interior of the housing 10 approximately two-thirds of the way up provides the demarkation between the upper and lower chambers 12 and 14. Actually, the flange 22 cooperates with a disklike divider member 86 constituting the top element of a rack assembly 24 which holds a flow device such as extraction cartridges 26. Although any separatory column, filter, or other device for establishing a flow path may be used, the extraction cartridge 26 may be that described in U.S. Pat. No. 4,214,993 issued July 29, 1980 to Forsythe et al. and entitled Apparatus for Separating Fluids. The upper surface of the flange 22 has an annular recess 28 formed therein adapted to accommodate a soft o-ring 30 which cooperates with the rack assembly 24 to provide the seal between the two chambers 12 and 14.

At the base of the interior of the housing 10 there is provided an extended inner flange 32 which acts as a dashpot cylinder as will be described. The flanges 22 and 32 may be formed of aluminum or stainless steel as desired.

To complete the description of the housing 10, the lid 20, also formed of a suitable rigid material such as aluminum or stainless steel, is generally disklike in configuration and sits flush against the top portion of the housing 10. Although an o-ring seal may be used, it has generally not been found to be necessary. As is seen most clearly in FIG. 4, a fluid distributor 34 is secured to the lower portion of the lid 20. A plurality of short links of tubing 36, each of a small inside diameter, are arranged radially about and in fluid communication with a manifold or chamber 35 (FIG. 4) in the distributor 34. One end of each tubing is fitted into a bore formed equi-angularly about the hub, the bore in each case extending to the hollow interior 35 of the distributor. Fluid is supplied to the manifold 35 of the distributor 34 via a bore 38 preferably formed directly through the lid 20, thence through suitable tubing 40 and a filter 42 to respective reservoirs 44 and 46. Appropriate solenoid valves 48 and 50, respectively, open and close the tubing or lines from the respective reservoirs to the filter 42 and the manifold 34. The length of the tubing links 36 is such that each link empties immediately above the location at which the extractor cartridges 26 are located, as will be described.

Vacuum lines 52 and 54 are connected through the wall 16 of the housing 10 to the upper and lower vacuum chambers in the interior of the housing. Thus the upper line 52 is connected to the upper vacuum chamber 12 and the lower line 54 to the lower vacuum chamber 14. Each of the lines 52 and 54 is controlled by suitable solenoid valves 58 and 60, respectively. The valves 58 and 60 may be dual throw valves. Thus the valve 58 may connect the line 52 either to the atmosphere or through a line 66 to a source of vacuum, designated in relative terms as −6, derived from a pressure regulator 68 and a vacuum pump 70. Similarly, the line 54 may be connected through the dual valve 60 either to the pressure regulator 68 or directly to the higher vacuum of the vacuum pump 70 via the line 72.

Each of the valves 48, 50, 58 and 60 are connected through suitable control wires 62 to a controller 74. The controller 74, in its simplest form, may be a simple rotary switch that will sequence to switch from one position to another the several valves. In the preferred form of the invention, however, the valves are opened and controlled under the control of a microprocessor which may be programmed according to the whim of the user to follow an almost infinite sequence of variable instructions. Since the particular microprocessor does not form a part of this invention, it will not be described further and is mentioned only by way of complete disclosure.

In accordance with a preferred embodiment of this invention, the first, second and third fluid flow paths are illustrated as being in the form of the extraction cartridge 26, a waste receptacle 94 and a recovery cup 96 are positioned in the rack assembly 24 seen most clearly in FIG. 1. This rack assembly 24 comprises a central support member or rod 80 which is inserted into a base disk 82 having a diameter slightly less than the inner diameter of the damping cylinder formed by the extended inner flange 32. In a typical unit that has been constructed, where the inner diameter of the damping cylinder is 14.2875 cm, the diameter of the base disk is 14.2748 cm, i.e., 0.0127 cm less. The purpose of this is to permit the base disk 82 to function as a dashpot acting against rapid vertical motion of the rack assembly by compressing the air present in the region 84 at the bottom of the housing 10. Since the air present may leak only through the narrow annular space between the periphery of the base disk 82 and the damping cylinder 32, the vertical movement of the rack assembly is cushioned in both upward and downward directions.

At the upper end of the rack assembly 24, there is a flexible divider or disk 86 which has a diameter slightly less than the inside diameter of the housing such that its peripheral portion may rest upon and be supported by the flange 22 and engage the o-ring 30 to provide a seal and separate the housing into the upper and lower vacuum chambers 12 and 14 described. A plurality of orifices are formed and located in a ringlike configuration in the disk 86 to provide a receptacle or retainer for the first fluid flow path such as that provided by the extraction column 26. The disk 36 preferably is formed to have a convexity, as illustrated, to enhance its switching function, as will be described. Similarly a mid-disk 90 is secured to the column or post 80 essentially midway between the upper flexible disk 86 and the base disk 82. Both the mid-disk 90 and the base disk 82, as well as the flexible disk 86, may be formed of a relatively rigid plastic. In the case of the upper disk 86, however, this plastic should be flexible, have a high stress fatigue, be resilient and yet inert to chemicals. Materials suitable for this purpose include nylon resin, acetal resin, polycarbonate, and polypropylene. While it is necessary only that the upper disk 86 flex, the base disk 82 is formed to have a thickness approximately twice that of the other disks. It is undesirable for the lower disk to flex. The mid-disk 90, although capable of flexure, need not do so and hence its thickness is not critical. The mid-disk 90, however, has inner and outer annular rings of orifices 95 and 97, respectively (FIG. 3), to hold rings of receptacles 94 and 96 constituting the second and third fluid flow paths, respectively. These flow paths may be embodied in an extraction application in the form of the waste cups 94 for the inner annular ring and recovery cups 96 for the outer annular ring.

The extraction cartridge 26, the waste cup 94 and the recovery cup 96 may be capable of being stacked for ease of storage and shipment as described by Forsythe et al. In any event, in a typical case the extraction cartridge 26 may include a resin bed 98. Each end of the resin bed is secured by means of a porous plug 100 to permit the passage of fluids therethrough and yet prevent the particles comprising the resin bed from becoming dislodged from position. The plugs 100 are somewhat larger than the inner diameter of the tube in which the resin bed is contained. The upper portion 102 of the extraction cartridge 26 is enlarged and tapered to provide a fluid reservoir, whereas the very top portion is enlarged still further to accommodate the introduction of a cap or plug (not shown). The lower end of the extraction cartridge is in the shape of a nozzle 108 to direct effluent fluids in a small diameter stream to one of the second or third flow paths in accordance with the fluid switching of this invention.

The waste cup 94 is also a tapered unit, the interior bottom portion of which has inwardly directed flanges (not shown) to maintain the lower end of the extraction column 26 properly positioned when they are nested prior to use. The waste receptacle itself is tapered with the upper portion enlarged to accommodate a cap (not shown). Finally, the recovery cup 96 is tapered with an enlarged upper portion to accommodate a cap (not shown). The extraction column, waste receptacle, and recovery are all constructed to be roughly the same upper diameter such that, with their taper, they may be stacked in a nested array as described by Forsythe et al. For storage, this nested array facilitates vapor sealing and maintains the extraction column moist during storage if required.

Figure 4:
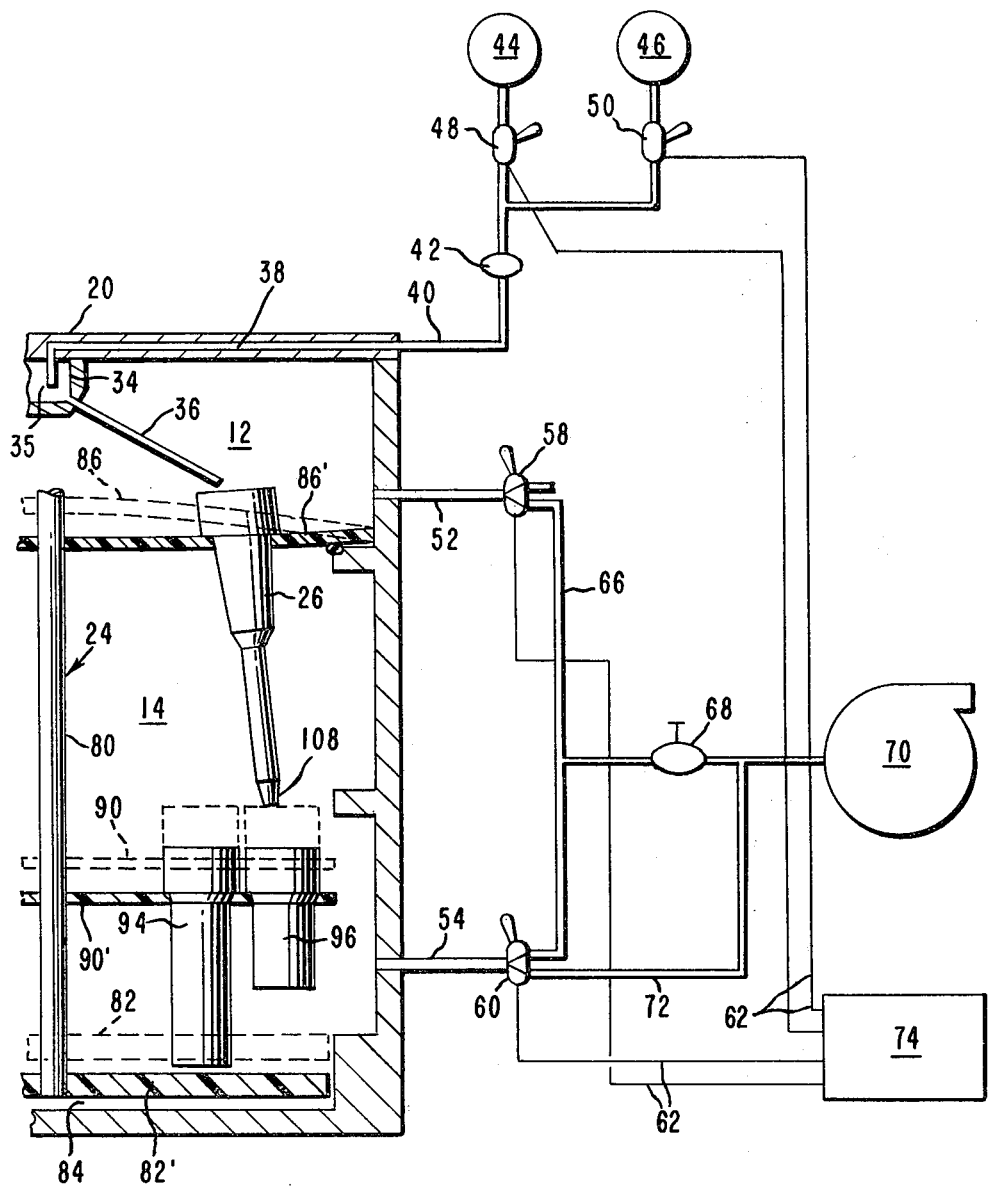
FIG. 4 is a partial cross-sectional elevation view showing schematically the vacuum controls which operate the fluid switching apparatus and depict the fluid switching apparatus in an operated condition.

The operation of this rack assembly 24 is most easily understood by reference to FIG. 4 and observing that if a vacuum is applied to the lower chamber 14, the disk 86 will collapse or concave at some predetermined pressure. As the disk collapses to the position 86', the lower tips 108 of the extraction cartridge 26 extend outward radially to shift their alignment from the waste cup to the recovery cup. This predetermined pressure is more easily controlled by varying the degree of convexity of the disk 86. Thus, index control may be achieved by manufacturing the disk to have a slight convex shape (approximately 5° although this value is not critical—convexities up to about 10° may be used). This convex shape tends to resist bending, up to some threshold of pressure, due to compressive loading and then suddenly collapses to effect the transition in a manner not unlike that of an oilcan. When the disk collapses as at 86', the rack assembly 24 including shaft 80 moved downwardly. This downward movement carries the mid-disk 90 and base disk 82 from the dotted line positions illustrated to the positions 90' and 82', the base disk 82' effecting the dashpot function described.

In a typical operation, a rack assembly, which may be disposable, is loaded with the extraction cartridges 26 suspended in the top disk 86 with the waste cup 94 in the inner ring of the mid-disk and the recovery cup 96 in the outer ring of the mid-disk 90. The entire rack assembly 24 is lowered into the housing 10 until the top disk 86 rests upon the flange 22. The lid 20 is placed on the housing and the controller 74 actuated according to the following sequence:

| | Condition | Valve Position |
|---|---|---|
| 1 | Sample - sample pulled through column | 58 to air<br>60 to 68<br>48, 50 closed |
| 2 | Solvent Intake (H₂O) | 58 to 68<br>60 to 68<br>48 open, 50 closed |
| 3 | Solvent through column (wash) | 58 to air<br>60 to 68<br>50, 48 closed |
| 4 | Shift (recovery bucket) | 58 to air<br>60 to 70<br>48, 50 closed |
| 5 | Solvent Intake (acetone etc.) and release from column | 58 to 68<br>60 to 70<br>50 open, 48 closed |
| 6 | Evaporate | 58 to air<br>60 to 70<br>48, 50 closed |

As may be seen from this chart, and with reference to FIGS. 1 and 4, after a sample is placed manually in each extraction cartridge 26, it is drawn through the column. While typically gravity will suffice for this purpose, in order to enhance the speed of the operation, a vacuum is applied to speed the transport of the sample through the extraction cartridge 26. To accomplish this, the valve 58 is switched thereby opening the upper chamber 12 of the housing to the atmosphere. Valve 60 is switched to the pressure reducer 68 to apply an intermediate vacuum of typically −6 (in relative members) to the lower vacuum chamber 14.

As a second step, a solvent from the reservoir 44 is applied through the distribution manifold 34 to each of the extraction cartridges. This is accomplished by opening the valve 48 allowing water or other solvent from the reservoir 44 to pass through the filter 42, the lines 38 and 40 to distribution manifold 34, thence to each of the links 36. Because each of the links 36 have a relatively small uniform inside diameter, fluid flow division is generally good and equally divides the flow from the manifold 34 to each of the extraction cartridges. The reservoir 44 need not be pressurized and the solvent flow may be initiated simply by switching the valve 58 to connect the head portion of the housing 10 to the intermediate vacuum −6 via line 66. Valve 60 is switched to apply this same vacuum to the lower vacuum chamber 14 via the line 54. The application of this vacuum in the lower chamber 14 is necessary only to ensure that the rack assembly 24 is not lifted from contact with the flange 22 by the application of the vacuum in the upper portion 12.

In Step No. 3, solvent is caused to flow through the column and wash any undesired components of the sample through the resin bed 98 into the waste receptacle 94. For this step, valve 58 is switched to atmosphere. Valve 60 remains unchanged, i.e., connected to the intermediate vacuum −6. The vacuum in the lower vacuum chamber pulls the fluid through the extraction cartridge and, because of the alignment of the extraction cartridge with the inner ring of receptacles, passes it to the waste receptacle 94.

In accordance with this invention, the first fluid flow path, the extraction cartridge 26, is shifted from alignment with the second fluid flow path, i.e., the waste receptacle 94, to the third fluid flow path, i.e., the recovery cup 96. To accomplish this, the valve 58 is opened to atmosphere. Valve 60 is switched in this case to apply the full vacuum −12 to the lower chamber. This increase in vacuum causes the disk 86 to collapse, into a flat or slightly concave configuration (FIG. 4), thereby shifting the lower tip 108 of the extraction cartridge radially outwardly into alignment with the recovery cup 96. Too rapid a movement of the disk 34, and the post 80, is prevented by the damping chamber 84. Hence the base disk acts as a piston being driven down into the damping cylinder 32. Because of the annular space provided, between the disk piston and the cylinder, air, even though at reduced pressure, can escape at a predetermined rate allowing the post to move more slowly downwardly preventing a snap action of the disk 34, and hence the lower tip 108 of the cartridge 26 moves outwardly at a deliberate pace.

In Step No. 5, a second solvent is drawn from the reservoir 46 to remove the sample components retained on the resin bed by opening the valve 50 and allowing a suitable solvent to pass through the filter 42 and the lines 38 and 40 through the distribution manifold and the tubes 36 to the respective extraction cartridges 26. Valve 58 is switched to apply an intermediate vacuum of −6 to the header region, thus enhancing fluid flow from the reservoir 46 and in most cases eliminating the need for pumping the fluid from the reservoir. Valve 60 remains switched with the full vacuum −12 applied to the lower vacuum chamber 14. This permits solvent to be drawn through the extraction cartridge 26 and passed into the recovery cup 96.

As a final step, the solvent in the recovery cup, with the desired sample component entrained therein, may be evaporated leaving only the dried sample component in the bottom of the recovery cup 96. This is accomplished by switching the valve 58 to the atmosphere and leaving valve 60 in its full vacuum position. Evaporation under vacuum conditions is quite rapid. Although any desired vacuum may be used within the realm of practicality, vacuums in the general ranges of 100 kPa. to 1 kPa. have been found satisfactory. The particular pressure used for the intermediate and full vacuum respectively are essentially a matter of choice. At the end of an extraction the vacuum source 70 may be disabled or disconnected, as by another valve (not shown) connecting the line 54 to atmosphere, and the disk 86 snaps back to its convex configuration, switching the first and second flow paths back into alignment.

An alternative embodiments of the invention, pumps may be used to transport the fluids from the reservoirs 44 and 46 and positive pressures may be applied in the header region 12 to force fluid through the extraction cartridge. The pressure in this case is increased still more to cause the flexure of the disk. In this instance the lower vacuum chamber 14 may be connected to atmosphere. The operation of the damping chamber 84 remains unchanged. In still another alternative embodiment, the pressure in the lower vacuum chamber 84 may be varied to enhance damping, i.e., before switching the flow paths, the lower vacuum chamber is connected to atmosphere.

It is apparent that multiple solvents may be passed through or to the various flow paths at any step. Also the particular use or configuration of the several flow paths is not critical. The significant feature to be noted is the ability to switch flow paths, enhance flow rate, and damp the switching rate using a relatively simple housing and rack. The rack or cartridge holder has an independent use in facilitating the holding and storage of separated sample components as well as facilitating the fluid switching operation.

I claim:

1. A method of switching the flow of a fluid from a first to second and third unconnected flow paths using a flexible, generally planar and horizontally disposed member defining a receptacle for removably positioning a first flow path, and first rack means positioned below the member for removably positioning second and third flow paths comprising the steps of:

removably mounting said first flow path in said flexure member with the inlet and outlet of the first flow path located on opposite faces of the member, positioning said second and third flow paths in the first rack means in side by side relation vertically below said first flow path with one of the second and third flow paths in flow alignment with said first flow path, and flexing said member to switch the flow alignment of said first flow path from the one to the other of said second and third flow paths.

2. The method of claim 1 which includes the step of aiding the passage of said fluid through the first flow path by subjecting the faces of the member and hence the inlet and outlet of the first flow path to different gas pressures.

3. The method of claim 1 wherein said member is flexed by enclosing the member and the flow paths in a gas tight housing with the member supported at its periphery by the housing and separating the housing into upper and lower sections, and changing the gas pressure in at least one of the sections to establish a pressure differential between the member faces.

4. The method of claim 2 or 3 wherein the gas is air.

5. The method of claims 1, 2 or 3 which includes the step of damping the flexure movement of said member in a sense perpendicular to the plane of said member.

6. The method of claims 1, 2 or 3 wherein said first flow path includes a separating column.

7. Apparatus for fluid switching comprising:

a flexible, generally planar and horizontally disposed member supported at its periphery, defining a receptacle for removably positioning a first flow device, first rack means positioned below the member for removably positioning second and third flow devices in side by side relation below said first device with one of said second and third devices being in flow alignment with said first device, and means to apply a force to said member, thereby to flex the member relative to its periphery and reposition said first device into flow alignment with the other one of said second and third devices.

8. The apparatus of claim 7 wherein said member has upper and lower faces each adapted to be subjected to a gas pressure and said means to apply a force comprises means to subject the faces to different gas pressures.

9. The apparatus of claim 7 which includes means to damp the flexing movement of said member.

10. The apparatus of claim 7 wherein said damping means includes a cavity and a disk connected to said member positioned to move pistonlike in said cavity.

11. The apparatus of claim 8, 9, or 10 wherein said receptacle is adapted to receive the first flow device in a gas tight relationship with the device extending through the device between the two faces and said member is a disk having an axis perpendicular to the disk, the first rack positioning the second and third flow devices radially of the axis.

12. The apparatus of claim 8 wherein said member is convex, thereby to resist flexure until a threshold pressure differential between the faces is achieved.

13. The apparatus of claim 11 wherein said member is housed in a closed chamber having an interior annular support ring for peripherally supporting said member, said ring and member effectively dividing said chamber into upper and lower sections.

14. The apparatus of claim 13 wherein said means to subject the faces of the member to different gas pressures include means to vary the relative gas pressure in said first and second sections by a first amount to draw fluid through said first flow device into one of said second and third flow devices, and by a second amount greater than said first amount to cause flexure of said member.

15. The apparatus of claim 14 which includes a second interior, annular ring forming a cylinder in the lower portion of said chamber and a disklike piston adapted to slide within said cylinder, said piston being linked to said member and to move with flexure of said member, said piston and cylinder trapping gas to resist rapid fixture of said member.

16. A support rack for manipulating test devices each having a fluid flow path comprising:

first and second disks interconnected in spaced vertical disposition, said first disk being capable of flexure along an axis perpendicular to the plane of the disk when the disk is supported at its periphery and having a first ring of receptacles each adapted to hold removably a first device, said second disk being below said first disk and having inner and outer rings of receptacles, corresponding in circumferential disposition to the receptacles of the first ring, each adapted to hold removably a second test device, said receptacles being located in said disks to that (a) with the first disk unflexed, the flow paths of corresponding test devices, positioned in the other one of said inner and outer rings of the second disk and said first disk's receptacles, are in flow alignment, and (b) with the first disk flexed, the flow paths of corresponding test devices, positioned in the other one of said inner and outer rings of the second disk and said first disk's receptacles, are in flow alignment.

17. The apparatus of claim 16 wherein said disks are spaced by a support rod at the center of each of said disks, and which includes a third disk secured to the rod below said second disk, said third disk providing a support base for said rack.

18. The apparatus of claim 16 or 17 which also includes a cylindrical vacuum housing for said rack, said housing having an inner annular flange adapted to engage the circumference of said first disk and hence support said rack within said housing.

19. The apparatus of claim 17 which also includes a cylindrical vacuum housing for said rack, said housing having an inner annular flange adapted to engage the circumference of said first disk and hence support said rack within said housing, said housing also having a second inner annular flange adapted to be coaxially closely disposed about the periphery of said third disk, thereby to cushion movement of said rack by compressing air between said third disk and said housing.

20. The apparatus of claim 19 or 17 which includes means to reduce the air pressure within said housing below said first flange.

21. The apparatus of claim 16 or 19 which also includes a distribution manifold in the upper portion of said housing for passing fluids to the location each of said openings.

* * * * *